United States Patent [19]

Gansow et al.

[11] Patent Number: 4,923,985

[45] Date of Patent: May 8, 1990

[54] PROCESS FOR SYNTHESIZING MACROCYCLIC CHELATES

[75] Inventors: Otto A. Gansow, Washington, D.C.; Krishan Kumar, Rockville, Md.

[73] Assignee: The United States of America as represented by the Department of Health & Human Services, Washington, D.C.

[21] Appl. No.: 198,537

[22] Filed: May 25, 1988

[51] Int. Cl.$^5$ .................. C07D 257/00; C07D 259/00
[52] U.S. Cl. ...................................................... 540/474
[58] Field of Search ........................................ 540/474

[56] References Cited

U.S. PATENT DOCUMENTS 2,186,464  1/1940  Mauersberger ..................... 540/474
3,979,379  9/1972  Siele ..................... 540/474
4,543,213  9/1985  Weitl et al. ..................... 540/474
4,578,517  3/1986  Johnson et al. ..................... 540/474

FOREIGN PATENT DOCUMENTS 197810  10/1978  United Kingdom ................ 540/474

OTHER PUBLICATIONS

Tsuboyama et al., Tetrahedron Letters, No. 16, pp. 1367–1370 (1970).

Primary Examiner—David B. Springer
Attorney, Agent, or Firm—Mishrilal Jain

[57] ABSTRACT

A process for synthesizing a 12 membered ring tetraaza macromolecule comprising. The process involves condensing an amide of ethylene diamine having a general formula A:

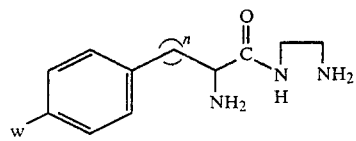

wherein n is an integer from 1 to 5 and w is a member selected from the group consisting of —NO$_2$, —NH$_2$, —NCS, —COOH, —OCH$_2$OOCH$_3$, —NCOCH$_2$—Z with Z being a member selected from the group consisting of Br and I with a nitrogen blocked active ester of a general formula B:

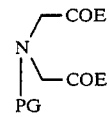

wherein PG is an amino protecting group and E is a leaving group.

6 Claims, 4 Drawing Sheets

PROCESS FOR SYNTHESIZING MACROCYCLIC CHELATES

BACKGROUND OF THE INVENTION

1. Field of the Invention

This invention relates to a process for synthesizing macrocyclic chelates. More specifically, this invention relates to 2-substituted 1,4,7,10-Tetraazacyclododecane-N,N',N'',N'''-tetraacetic acid, and 2-substituted 1,4,7,10-Tetraazacyclododecane, and analog macrocycles.

2. Description of the Background Art

Macrocycles have been studied for their usefulness as chelates for numerous metal ions that have therapeutic, diagnostic, or other uses. A macrocycle of particular usefulness as a chelate is the 1,4,7,10-Tetraazacyclododecane-N,N,N,N-tetraacetic acid (DOTA). DOTA compounds have been linked to biomolecules to form delivery systems for the chelated metal ion to specific sites within an organism. Processes to synthesize these compounds typically result in yields of 1 percent or less of the desired compound from the starting material.

U.S. Pat. No. 4,678,667 to Meares et al., discloses a macrocyclic bifunctional chelating agent. The chelating agents of this disclosure can include DOTA compound that is a Cu(II) chelate. The usefulness of the chelating agent is limited to the effects of the copper metal ion. The process of this disclosure gives low and not always reproducible results.

An earlier U.S. Pat. No. 4,622,420 to Meares et al. disclosed bifunctional chelating agents of the acyclic ligand ethylene diamene N,N',N'',N'''-tetraacetic acid (EDTA) useful for binding metals other than copper such as Indium. These compounds are useful for imaging of tumors.

U.S. Pat. No. 4,652,519 to Warshawsky et al., discloses bifunctional chelating agents and process for their production. The compounds disclosed in this patent are analogoues of EDTA. These compounds are used to chelate metal ions and are linked to haptens to provide specific site selection within an organism. The compounds of this patent are offered to provide an improved substituent for the EDTA compounds such as those disclosed in the Meares et al. patent discussed above.

U.S. Pat. Nos. 4,454,106 and 4,472,509 to Gansow et al., respectively disclose the use of metal chelate conjugated monoclonal antibodies and the specific metal chelate conjugated monoclonal antibodies. These disclosures provide compounds and methods for treating cellular disorders. Radiometal chelate conjugated monoclonal antibodies specific to a target cell are used to deliver alpha, beta, or Auger electron emitting metal ions. These disclosures are not related to DOTA compounds.

The value of having a ligand conjugate to chelate metal ions for therapeutic, diagnostic, or other uses is of commercial importance. This commercial importance is created by the fact that many metal ions have desirable characteristics for these various uses, but the delivery systems for the metal ions lack specificity to target cells or do not adequately bind the metal ions. Examples of the usefulness of specific metal ions are as follows.

The usefulness of radionuclide materials in cancer therapy is disclosed in the article, Kozak et al., "Radionuclide-conjugated monoclonal antibodies: A Synthesis of Immunology, in Organic Chemistry and Nuclear Science" *Trends in Biotechnology.* 4(10):259–264 (1985). This article discusses the use of antibody conjugates to deliver either alpha or beta radiation. The value of alpha radiation from bismuth-212 in radionuclide therapy is further discussed in the two articles, Kozak et al., "Bismuth-212-labled anti-Tac monoclonal antibody: Alpha-particle-emitting Radionuclides as Modalities for Radioimmunotherapy" *Proc. Natl. Acad. Sci. U.S.A.* 83:474–478 (1986) and Gansow et al., "Generator-produced Bi-212 Chelated to Chemically Modified Monoclonal Antibody for Use in Radiotherapy" *Am. Chem. So. Symposium Series* 15:215–227 (1984).

Examples of other uses for chelated metal ions are disclosed in the following articles. Magerstadt et al., "Gd(DOTA): An Alternative to Gd(DPTA) as a $T_{1,2}$ Relaxation Agent for NMR Imaging or Spectroscopy" *Magnetic Resonance in Medicine* 3:808–812 (1986), discloses the usefulness of gadolinium as a relaxation agent for NMR imaging. The article, Spirlet et al., "Structural Characterization of a Terbium(III) Complex with 1,4,8,11-Tetraazacyclotetradecane-1,4,8,11-tetraacetic Acid. Lanthanide Ions and the Conformation of the 14-Membered Macrocyles" *Inorganic Chemistry* 23(25):4278–4283 (1984), discloses the usefulness of the lanthanide chelates.

The industry is lacking an efficient process for synthesizing a DOTA chelate in high yields and that has desirable chelating qualities for numerous metal ions.

SUMMARY OF THE INVENTION

The invention is a process for synthesizing a 12 membered ring tetraaza macromolecule. The process involves condensing an amide of ethylene diamine having a general formula A:

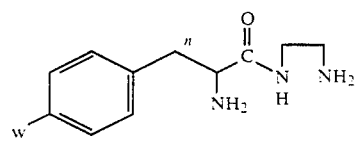

with a nitrogen blocked active ester of a general formula B:

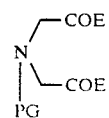

The process synthesizes a compound having a general formula I:

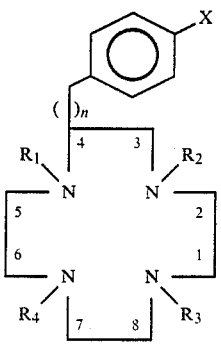

wherein
$R_{1-4H}$ is —CH$_2$COOH;
n is 1 to 5;
X is a member selected from the group consisting of —NO$_2$, —NH$_2$, —NCS, —NCOCH$_2$—Z with Z being a member selected from the group consisting of Br and I —COOH; —OCH$_2$OOCH$_3$
and M is a metal ion being a member selected from the group of elements consisting of Bi, Pb, Y, Cd, Hg, Al, Th, Sr, and Lanthanides.

DETAILED DESCRIPTION OF THE INVENTION

The compound produced by the the process of this invention is a substituted DOTA represented by the general formula I shown above or specifically by compound X of FIG. 1. Compound X can subsequently be converted to other substituted DOTA compounds, but compound X is the parent compound for such other compounds. The general formula is a 12 membered ring tetraaza macromolecule with the nitrogens in the 1, 4, 7, and 10 positions. Each of the nitrogens is "ribbed" by an ethylene group.

Figure 1:
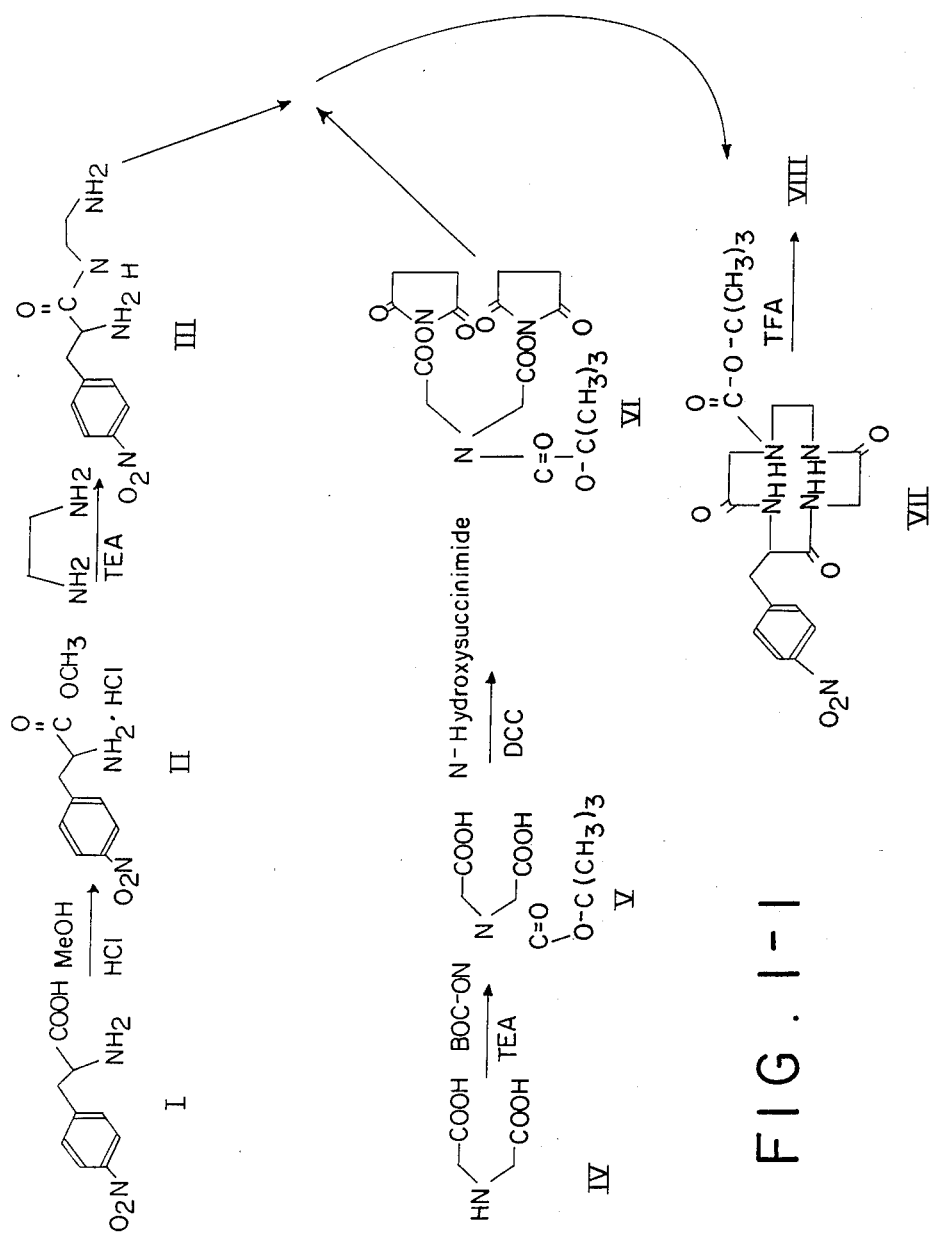
FIG. 1 illustrates a chemical pathway of the preferred embodiment of the invention.

The substituted DOTA ligand represented by compound X of FIG. 1 complexes metals. Metal complexes are formed by placing the DOTA into solution with an appropriate metal salt having the metal to be chelated. Metal salts have to be selected so as to prevent the hydrolysis of the metal. Also, reaction conditions in an aqueous medium have to be chosen such that the metal it not hydrolyzed. For example, a lead nitrate complex, bismuth iodide complex, or yttrium acetate salts can be used to form a metal chelate with lead, bismuth, or yttrium, respectively. General examples of suitable salts include any soluble divalent metal complex or any trivalent metal complex that is not hydrolyzed at pH 4 or below. Thorium requires the use of iodide salt, specifically. The most desirable metal ions for chelation with general formula 1 are members from the group consisting of bismuth, lead, yttrium, cadmium, mercury, actinium, thorium, strontium, and any of the elements of the lanthanide elements. The most desirable elements of the lanthanide series are gadolinium, for use in NMR imaging and as a relaxation agent in NMR imaging, and terbium and europium because of their use as chromophores in time resolved fluorescence spectroscopy. These fluorescent compounds can be useful in an in vitro diagnostic assay where a fluorescent assay is used rather than a radioactive amino assay.

The X substituent of general formula is desirably a substituent that conjugates the compound with haptans. This substituent is desirably a free-end nitro group which can be reduced to an amine. The amine can then be activated with a compound such as thionyl chloride to form a reactive chemical group such as an isothiocyanate. An isothiocyanate is preferred because it links directly to amino residues of a hapten such as a monoclonal antibody. The amiline group can be linked to an oxidized carbohydrate on the protein and, subsequently, the linkage fixed by reduction with cyanoborohydride. The amino group can also be reacted with bromoacetyl chloride or iodoacetyl chloride to form —NHCOCH$_2$Z with Z being bromide or iodide. This group reacts with any available amine or sulfhydryl group on a hapten to form a stable covalent bond. If tyrosine is used in the formulation of the macromolecule a carboxylic acid or methoxycarboxylate group can be in this position of the compound. The most desirable substituents for this position are members selected from the group consisting of —NO$_2$, —NH$_2$, —NCS, —COOH, —OCH$_2$COOH, and —NHCOCH$_2$—Z with Z being a member selected from the group consisting of bromide and iodide. The preferred substituent for this position is —NCS.

The haptens suitable for linking with the substituent at the X position of general formula I can vary widely. The most desirable haptens are members selected from the group consisting of hormones, steriods, enzymes, and proteins. These haptens are desirable because of their site specificity to tumors and/or various organs of the body. The preferred hapten for use in treating cellular disorders or various disease conditions is a monoclonal antibody.

The compounds synthesized by the process of this invention can have n equal an integer from 1 to 5. In the preferred embodiment of the compounds, n equals 2. It is desirable for n to equal 2 versus 1 because the chelating ligand is further separated from the antibody and has more rotation. The increased free rotation allows a metal to chelate with the macromolecule more easily. When n is 3 or greater, the synthesis of the compound becomes lengthy.

FIG. 1 illustrates the preferred reaction pathway or process for forming the compound of this invention. This reaction results in a compound of general formula I wherein n is 1. If n is to equal 2, an additional methylene group would be present between the alpha amino carbon and the aromatic group. This compound is 2-amino-4-nitrophenylbutyric acid.

The process for synthesizing a compound according to this invention first provides a triamine with a substituent is in the 2-position. The embodiment of FIG. 1 has a methylene [n = 1] as the initial substituent for linkage. The preferred embodiment has a phenyleythylene group. The process then provides a tetraaza macromolecule having the substituent in the 2 position. Alkylation with bromoacetic acid to form the four carbon to nitrogen bonds of the carboxymethylene substituents at the R1, R2, R3, and R4 in the general formula.

The process of FIG. 1 reacts p-nitrophenyl alanine with methanol and hydrochloric acid to form the ester compound II. This ester is reacted with ethylenediamine in the presence of triethylamine to remove the hydrochloride salt of the ester formed in compound II. The condensate of the amide of the ethylenediamine adduct or compound III is subsequently reacted with a diactive ester or compound VI to form a cyclic product or compound VII.

The desired diactive ester VI is formed sequentially from amidodiacetic acid for IV of FIG. 1. The amine is first blocked by using the reagent BOC-ON or any other suitable blocking agent, such as FMOC, in the presence of triethylamine which serves to deprotonate the starting material. The subsequent nitrogen blocked diacetic acid V or other such nitrogen blocked compound is then coupled to N-hydroxysuccinimide, or any other suitable compound such as phenols, or N-hydroxydicarboximides which forms a reactive ester. The choice of compounds which form active esters or blocking groups is within the scope of the art. The coupling is done by dicyclohexylcarbodiimide or "DCC". This step produces the nitrogen blocked active ester or compound VI.

Ring formation under high dilution conditions between amino acidamide or compound III with the nitrogen blocked active ester of Compound VI then occurs. This condensing step forms the triamide macrocycle or compound VII. Compound VII is produced in very high yield. The yield is typically at least about 80 percent. The yield more desirably is between about 80 percent to about 95 percent.

The synthesis of the macrocycle of compound VII may be accomplished by two pathways. The amine nitrogen of compound VII is deblocked with trifluoroacetic acid or "TFA". This forms the TFA salt of the triamide macrocycle or compound VIII. This compound is reduced with borane/tetrahydrofuran or THF. The resulting borane adduct is cleaved by hydrochloric acid to form the substituted tetraazamacrocycle of compound IX. This tetraazamacrocycle can then be alkylated with haloacetic acid in the presence of base to form a nitrobenzyl DOTA or compound X. Alternatively, compound VII can be reduced with borane/THR and reacted with hydrochloric acid to form compound IX directly. This alternative pathway produces slightly poorer yields.

The nitro group of compound X can be reduced with hydrogen over platinum on a carbon catalyst to produce the amino group or the aminobenzyl DOTA depicted as compound XI. Compound XI can then be reacted with thiophosgene to produce the isothiocyanate or compound XII.

The reaction steps described above to produce compounds X, XI, and XII are known. The novel feature of the process of FIG. 1 is the cyclization procedure. The conversion reaction of compound IV with compound VI to form the macrocycle and the full reduction of the macrocycle to produce compound X produces the unexpected results of very high yields compound X.

In its preferred embodiment the coupling of an isothiocyanate chelate of compound XII of FIG. 1 is done by direct conjugation of the isothiocyanate with a free amino group found in many residues of proteins, enzymes or other compounds such as certain hormones. An example of this situation with a hormone is found with the free amino group provided by the epsilon amino group of the lysine or the terminal amino group as the hormone peptide chain. Any free amino group can react with the isothiocyanate to form a thiourea linkage which is covalently coupled and irreversible. The use of a steriod as a hapten requires that an amino function be present in the steroid.

An advantage of the amine derivative chelate of compound XI of FIG. 1 is that, when coupling to proteins and, in particular, when coupling to antibodies, the carbohydrate of the antibody can be oxidized prior to the coupling reaction. The amine reacts with the aldehyde that is formed on the protein. This aldimine formed can be reduced by cyanoborohydride to form a covalent secondary amine linkage to the antibody in a position that is site specific. This position is away from the binding site of the FAB'2 part of the monoclonal antibody.

The selection and use of amino protecting groups and leaving groups with the compounds of this invention are within the skill of the art. Amino protecting groups suitable for this invention are disclosed by Greene, *Protective Groups in Organic Synthesis* (New York: John Wiley & Sons) Chapter 7. Leaving groups are disclosed by Bodanszky, *Principles of Peptide Synthesis* (Berlin: Springer-Verlag) Chapter II (1984).

EXAMPLE 1

This example represents the preferred embodiment of the invention. FIG. 1 represents the chemical pathway of this example. The Roman numerals used in this example refer to the corresponding compounds in FIG. 1.

Compound I was commercially obtained from U.S. Biochemicals, Cleveland, OH. It was converted to the corresponding amino acid amide of ethylenediamine (III) as described in detail in Brechbiel, et al. *Inorganic Chemistry*, 1986, 25, 2722-2781.

The protected carbamate (V) was prepared by reaction of 6.65 g (0.05 mole) of imidodiacetic acid (IV) (Eastman Kodak, Rochester, NY) with 13.54 g of BOC-ON (Aldrich Chemical Co., Milwaukee, WI) in 150 ml of 50% aqueous dioxane in the presence of 20.9 ml triethylamine (Aldrich Chem. Co.). After two hours, the solution clarified but the reaction was allowed to stir overnight at room temperature. After addition of 50 ml water, the reaction was extracted three times with 100 ml portions of ethyl acetate to remove phenylacetonitrile by-product and the aqueous layer retained. After lowering the pH of the aqueous solution to pH 2 with 3N HCl, the solution was cooled to 0°-4° C. and thrice extracted cold with 100 ml portions of ethyl acetate. The organic layer extracts were dried over $MgSO_4$ and, after filtration, were reduced to 10-15 ml volume on a rotary evaporator. Addition of 250 ml petroleum ether produced the solid product (V) which was collected and dried. The yield was 10.0 g or 86%.

To prepare (VI), 7.0 g (0.03 mole) of (V) was dissolved in 100 ml dry ethyl acetate, cooled to 0° C. and 5 ml dry ethyl acetate containing 13 g (0.063 mole) dicyclohexylcarbodiime (DCC) added. Immediately thereafter, 7.0 g N-hydroxysuccinimide (Sigma Chem. Co., St. Louis, MO) was added as the solid. A drying tube was attached and the mixture stirred cold for 30 minutes and thereafter let to stir at room temperature for 4-5 hours at which time a precipitate formed. Then 0.5 ml 7M acetic acid was added to quench the reaction. The solid was collected by filtration, and the filtrate taken to dryness to provide 2.5 g of (VI). The solid was partially dissolved in 800 ml boiling ethyl acetate and filtered hot to remove the dicyclohexylurea side product. This filtrate was cooled to room temperature and a solid residue formed which was also removed by filtration. Reduction of the last filtrate to dryness provided 8.9 g of (VI). Yield of (VI): 11.4 g or 88%. A chemical ionization mass spectrum of (VI) gave an m+1 peak at 428 amu. A portion nmr spectrum in CDCl₃ showed four singlets at 4.51(2H), 4.35(2H), 2.83(8H), 1.50(9H) ppm.

For the preparation of (VII), a flame dried 5 L three neck round bottom flask was fitted with two 250 ml constant addition funnels 4 L dry dioxane added and the vessel maintained at 60° C. One addition funnel was charged with 250 ml dioxane containing 4.23 g (VI). To the other addition funnel was added 2.53 g (III) dissolved in 75 ml dimethylformamide and 175 ml dioxane. Dropwise addition over 8 hours followed by 15 hours stirring formed (VII). To isolate the product, the reaction solution was taken to dryness on a rotary evaporator and the solid completely dissolved in a 700 ml ethyl acetate, 250 ml water biphasic mixture. Thereby the n-hydroxysuccinimide by-product was selectively taken up in the water and the aqueous layer separated off by use of a separatory funnel. The ethyl acetate extract was then twice washed with 250 ml water. After washing, the ethyl acetate layer was free of N-hydroxysuccinimide as verified by thin layer chromatography on silica gel with 4:1::CHCL₃:methanol. All water washings were combined and extracted twice with 200 ml of ethyl acetate. This 400 ml ethyl acetate was combined with the similar 700 ml extract from above, dried over sodium sulfate, filtered, and taken to dryness to yield the product (VII). The yield was 4.1 g or 91%.

For the preferred method for preparation of (IX), 3.4 g (VII) was dissolved in 30 ml trifluoroacetic acid (TFA). After 3 hours, the solution was taken to an oily residue on a rotary evaporator. Addition of 50 ml ethyl acetate precipitated the product (VIII). Then the TFA remaining and the ethyl acetate are removed by rotary evaporation. An additional 50 ml ethyl acetate was added to precipitate the pure product which was collected by filtration and dried. The yield was 2.85 g, or 81%. CIMS: m+1=350 amu; m+1-NO=320 amu. Proton nmr in d6-DMSO (shifts in ppm vs TMS): aromatics, 8.1(2H), 7.5(2H); methine, 4.5(1H): methylenes, 2.52-3.8(10H).

To reduce the triamide (IX), diborane in THF was employed. In a three neck round bottom flask under Argon gas was added 40 mg (VIII) in 10 ml THF. After cooling to −10° C., 0.66 ml 1M BH₃ in THF was added. The solution was brought to room temperature with stirring and then refluxed for 20 hours. After cooling to 0° C., 5 ml methanol was added to kill the remaining borane. Next, the reaction solution is taken to dryness and dissolved in 10 ml methanol saturated with HCl gas and 5 ml concentrated HCl and refluxed for 18 hours. After removal of solvent, the residue is taken up in 10 ml absolute ethanol and set at 4° C. overnight upon which the product (IX) is precipitated. The product is collected by filtration, washed with ether and dried. The yield was 20 mg, or 55%. CIMS: m+1=308 amu, m=1-NO=278. Proton NMR in D₂O, pH 1.5, shifts vs TSP. Aromatics, 8.24(2H), 7.52(2H); methine, 4.5(1H); methylenes, 2.5-4.0(16H). A small amount of aniline side product is also detected.

The conversion of (VII) to (IX) may also be done directly by reaction with diborane and an HCl work-up. Thereby, 898 mg of (VII) is placed in 75 ml THF under argon in a three neck flask. After cooling to −10° C., 7 ml 1M BH₃/THF is added and the reaction brought to room temperature. After refluxing for 3 hours, the reaction is cooled to 0° C. and 20 ml methanol added slowly. The solvent is stripped and the residue taken up in 30 ml ethanol saturated with HCl gas and 15 ml concentrated HCl and refluxed for 18 hours. After removal of solvents, the residue is treated as described in the paragraph above. CIMS and proton nmr spectra were identical to those obtained for (IX) above.

Conversion of (IX) to (X) was accomplished by the methods described by Dereux, J. F., Inorganic Chemistry, 1980, 19:1319–1324 and Stetter, H. and Frank W., Angew. Chem. (Intern, Ed.) 1976, 15, 686.

COMPARATIVE EXAMPLE A

Figures 1, 2:
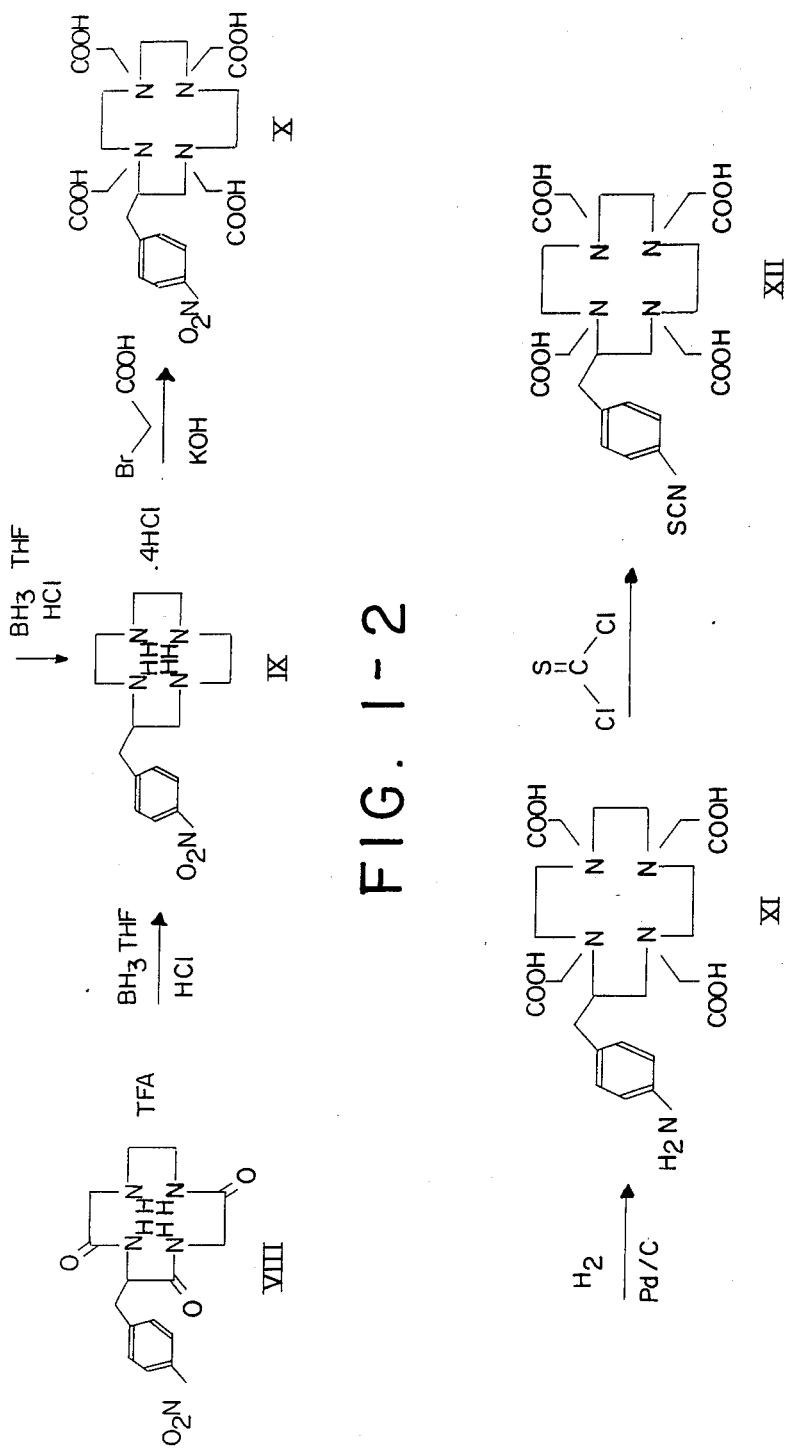
FIG. 2 illustrates a comparative chemical pathway for the desired compounds X through XII of FIG. 1.
Figure 2:
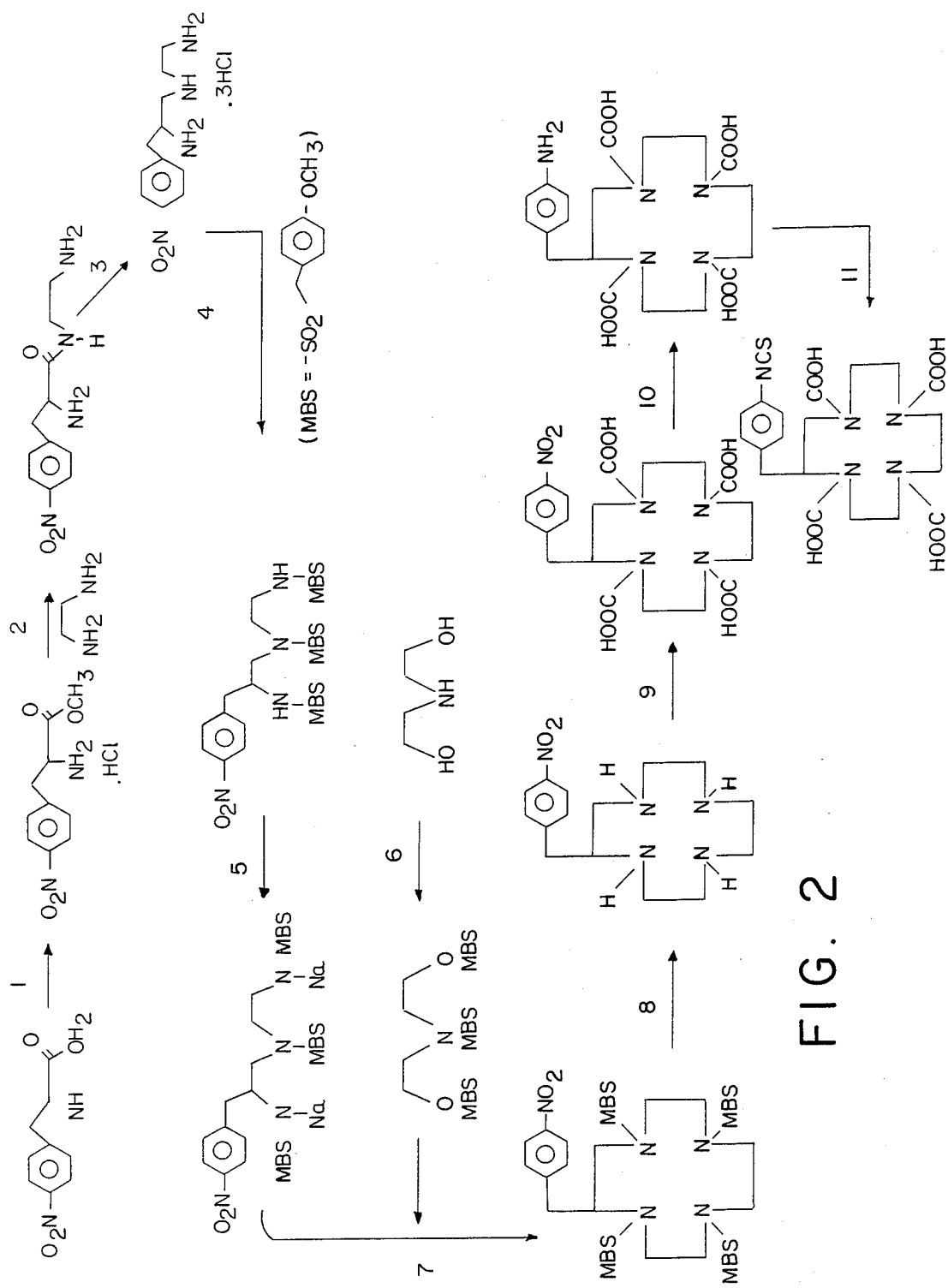

This comparative example demonstrates a process for synthesizing compounds X through XII of FIG. 1. The process of this comparative example is approximately equivalent to the process disclosed by Meares et al. FIG. 2 is an illustration of the chemical pathway of this process and is a synthesis of 2-p-isothiocyanatobenzoyl-1,4,7,10-tetraazacyclododecane-1,4,7,10-tetraacetic acid (p-SCN bz DOTA)

Steps 1–3

Preparation of 2-(p-nitrobenzyl)-diethylenetriamine trihydrochloride.

Step 4

Reaction of 2-(p-nitrobenzyl)-1-diethylenetriamine trihydrochloride with p-methoxybenene-sulfonyl chloride to N,N',N''-tris(p-methoxybenzenesulfonyl)-2-(p-nitro-benzyl)-diethylenetriamine

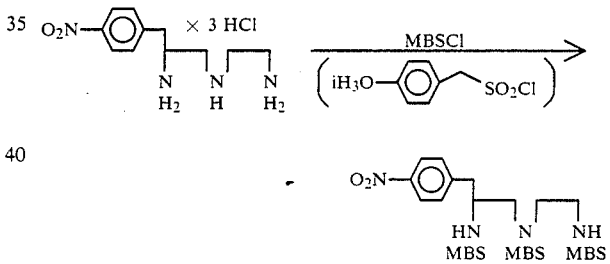

4 g of the triamine trihydrochloride and 2.76 g NaOH were dissolved in 70 ml H₂O (at 0° C.), then a solution of 7.61 g MBSc1 in 40 ml diethylether was added dropwise at this temperature. The mixture was vigorously stirred at room temperature for 20 hours. The yellow, sticky product was filtered from the solution, washed several times with water and once with CH₃OH and vacuum dried. The yield was 7.8 g or 86% of a white (slightly yellow) solid. Characterization by 1H-nmr.

Step 5

Reaction of N,N',N''-tris(p-methoxybenzenesulfonyl)-2-(p-nitrobenzyl)-diethylenetriamine with sodium ethylate to 1,7disodium-1,4,7,-tris-(p-methoxybenzenesulfonyl)-2-p-nitrobenzyl)-1,4,7-triazaheptane

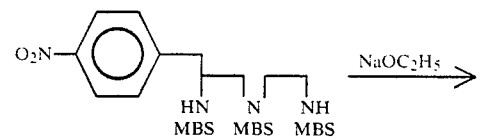

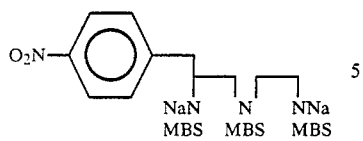

0.45 g Na were dissolved in 10 ml dry ethanol. The triamine compound was partly dissolved in 80 ml dry ethanol and, at room temperature, the NaOET-solution was added dropwise. After 1 hour, the mixture was refluxed for 1½ hours, then the ethanol was removed and the product vacuum-dried. The yield was 7.66 g or 93%. Characterization by $^1$H-nmr.

Step 6

Reaction of diethanolamine with p-methoxybenzenesulfonylchloride to 1,4,7-tris-(p-methoxybenzenesulfonyl)-1,7dioxa-4-azaheptane

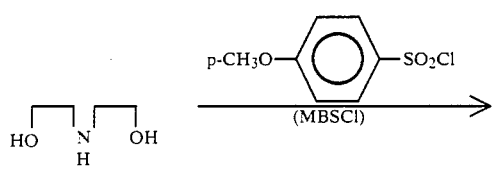

13.2 g MBSCl were dissolved in 50 ml CH$_2$Cl$_2$ and 4.74 g pyridine. At 0° C., 2.1 g diethanolamine were added dropwise. The mixture was stirred at room temperature for 20 hours (green solution). The solution was extracted four times with 100 ml ag HCl (pH2) each. The organic phase was dried over MgSO4, filtered and the solvent removed in vacuum. The resulting yellow oil was purified by dissolving in CHCL$_3$/ET$_2$O, washing with CH$_3$OH, and vacuum-drying. A pyridine-free product (yellow oil) was obtained. Characterization by $_1$H-nmr. The yield was 12 g or 91%.

Step 7

Hybridization of 1,7-disodium-1,4,7-tris-(p-methoxybenzenesulfonyl)-2-(p-nitrobenzyl)-1,4,7-triazaheptane with 1,4,7-tris-(p-methoxybenzenesulfonyl)-1,7,dioxa-4-azaheptane to 1,4,7,10-tetratris-(p-methoxybenzenesulfonyl)-2-(p-nitrobenzyl)-1,4,7,10-tetraazacyclododecane

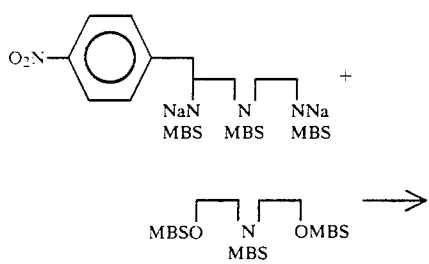

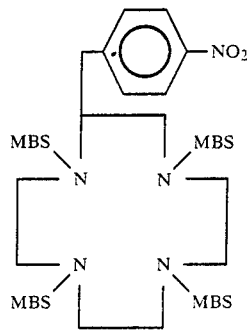

7.66 g of the disodium salt was dissolved in 50 ml N,N-dimethylformamide (DMF) at 90° C., and a solution of 6.03 g of the diethanolamine derivative in 50 ml DMF were added dropwise. After stirring at 90° C. for 30 hours, the mixture was cooled to room temperature and 100 ml H$_2$O were added. The dark solid precipitate resulting was removed after stirring for another 24 hours at room temperature. The precipitate was washed with water and freeze-dried. Characterization by $_1$H-nm and $_{252}$Y-PDMS. The yield was 5.8 g or 60%.

Step 8

Removal of the p-methoxybenzenesulfonyl protecting groups with methanesulfonyl acid/amisol to prepare 2-(p-nitrobenzyl)-1,4,7,10-tetraazacyclodecane (p-NO$_2$ bz cyclen) tetrahydrochloride

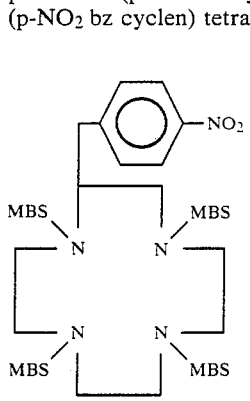

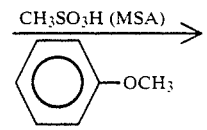

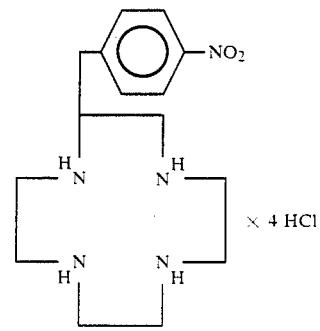

4.9 g of the protected macrocycle were put into a mixture of 90 ml MSA and 4.75 ml amisole and stirred at 90° C. for 20 hours. After cooling at room temperature, the solution was washed several times with 700 ml diethyl ether each, then taken into 100 ml H$_2$O/HCl at pH 1.5 and the aqueous solution was extracted 5 times with 100 ml diethyl ether each. The aqueous phase was run over an AG 1×8 (OH-form) amion exchange column (Bio Rad) with a three-fold excess of column material (batchwise) The eluates were combined, again acidified to pH$^Z$ and again extracted with diethyl ether (3×50 ml). NMR spectra showed a product that still contained one MBS group per macrocycle. This was removed by priming the 1.5 g of product obtained into 15 ml MSA+0.75 ml amisole and stirring the mix at 95° C. for 20 hours. The cooled solution was again treated with diethyl ether, then taken into 10 ml H$_2$O and extracted 4 times with 150 ml H$_2$CL$_2$ followed by running the aqueous solution over an AG 1×8 (OH)-column as described above. Again, the eluate was taken into ag. HCl and extracted once with CH$_2$Cl$_2$. Out of the aqueous solution, 760 mg pure product were obtained and characterized by$^1$H-nmr and $^{252}$Cf-PDMS.

COMPARATIVE EXAMPLE B

Figure 3:
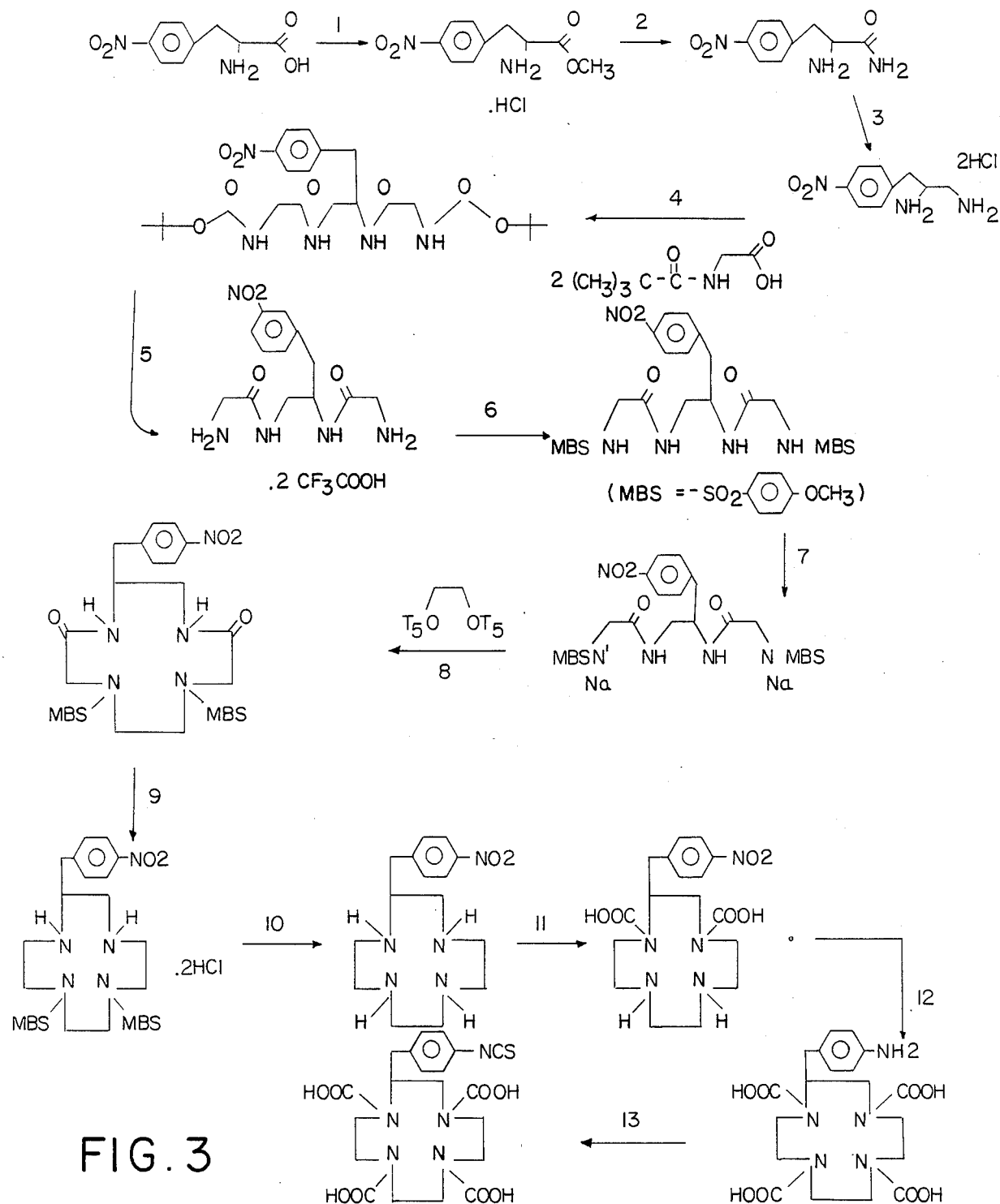
FIG. 3 illustrates a comparative chemical pathway involving a peptide to produce the desired compounds X through XII of FIG. 1.

This comparative example demonstrates a process for synthesizing compounds X through XII of FIG. 1. This comparative example involves a peptide type route. This process provides a better yield of the initial cyclized product. The reaction sequence is disclosed in FIG. 3 and is a synthesis of 2-p-Isothiocyanatobenzyl-1,4,7,10-tetraazacyclododecane-1,4,7,10-tetraacetic acid (p-SCN bz DOTA)

Steps 1-3
Reaction of 2-(p-nitrobenzyl)-ethylenediamine.

Step 4
Reaction of 2-(p-nitrobenzyl)-ethylenediamine with N-tert-butoxycarbonyl glycine ("boc-gly") to the substituted dipeptide "boc-gly-(2p No$_2$ bzen)-gly-boc"

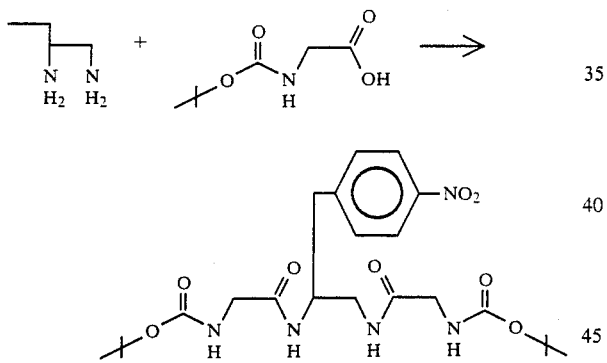

1.04 g 2-(p-nitrobenzyl)-ethylenediamine, 1.19 ml triethylamine, 1.36 g N-tert butoxycbonylglycine, 0.95 g 1-hydroxybenzotriazole, and 1.75 g dicyclohexylcarbodiimide were each dissolved in 10 ml N,N dimethylformamide (DMF) and the solutions were mixed. The mixture was stirred at room temperature for 4 days, then filtered to remove the dicyclohexylurea. After rotaevaporation of the solvent, a sticky residue was obtained. It was transferred to a Soxhlet - extractor and continuously extracted with ethylacetate for 20 hours. The resulting red solution was extracted three times with 250 ml 0.5N HCl each, followed by an extraction with 150 ml saturated ag. NaCl solution, again followed by three extractions with 200 ml 5 percent ag. NaHCO$_3$ solution and another extraction with 150 ml saturated ag. NaCl solution. The organic phase was derived over MgSO$_4$, filtered, and evaporated to a greyish solid, which was titrated with 0.5N HCl over night to remove the starting material. After filteration and freeze-drying, 1.4 g (71 percent yield) of the product were obtained. Characterization by 1H-nmr in Om50.

Step 5
Deprotection of "boc-gly-(2pNo$_2$bzen) gly-boc" with trifluoroacetic acid

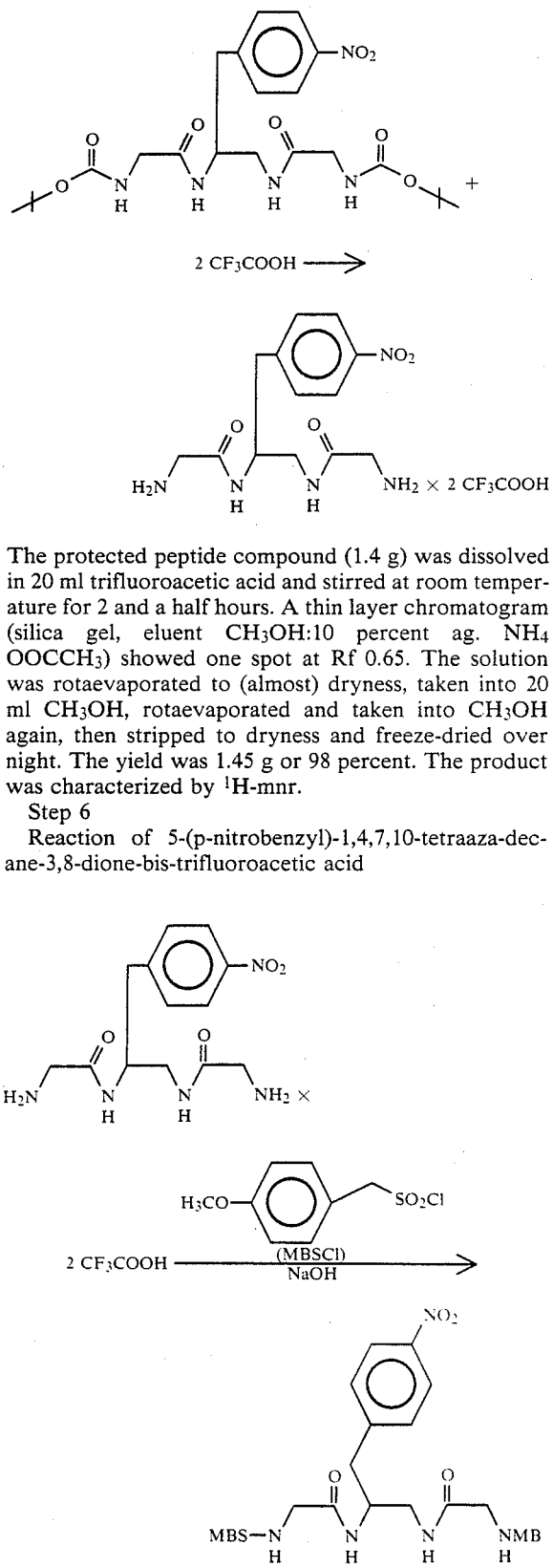

The protected peptide compound (1.4 g) was dissolved in 20 ml trifluoroacetic acid and stirred at room temperature for 2 and a half hours. A thin layer chromatogram (silica gel, eluent CH$_3$OH:10 percent ag. NH$_4$ OOCCH$_3$) showed one spot at Rf 0.65. The solution was rotaevaporated to (almost) dryness, taken into 20 ml CH$_3$OH, rotaevaporated and taken into CH$_3$OH again, then stripped to dryness and freeze-dried over night. The yield was 1.45 g or 98 percent. The product was characterized by $^1$H-mnr.

Step 6
Reaction of 5-(p-nitrobenzyl)-1,4,7,10-tetraaza-decane-3,8-dione-bis-trifluoroacetic acid salt with p-methoxybenzenesulfonyl chloride to 1,10-bis-(p-methoxybenzenesulfonyl)-5-(p-nitrobenzyl)-1,4,7,10-tetraazadecane-3,8-dione

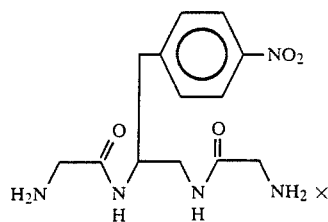

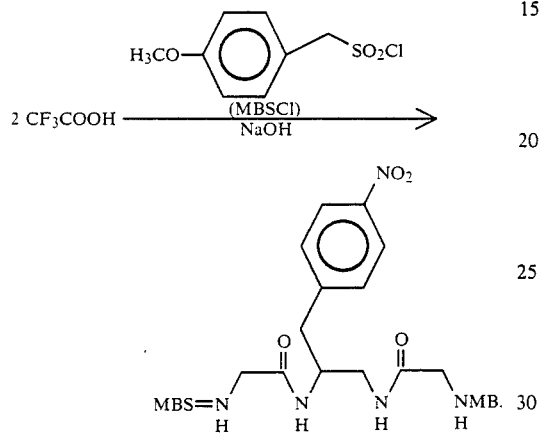

The tetraaza compound (1.45 g) and 0.45 g NaOH were dissolved in 40 ml H₂O. At 0° C., a solution of p-methoxybenzenesulfonyl chloride in 5 ml diethyl ether was added dropwise under vigorous stirring. The mixture was stirred at room temperature for 20 hours. A voluminous precipitated was separated from the aqueous solution, washed with large amounts of water, and freeze-dried over night. The yield was 1.5 g or 80 percent. Characterization by ¹H-nmr.

Step 7

Reaction of 1,10-bis-(p-methoxybenzenesulfonyl)-5-(p-nitrobenzyl)-1,4,7,10-tetraazadecane-3,8-dione with sodium ethylate to 1,10-disodium-1,10-bis-(p-methoxy-benzene-sulfonyl)-5-(p-nitrobenzyl)-1,4,7,10-tetraazadecane-3,8-dione

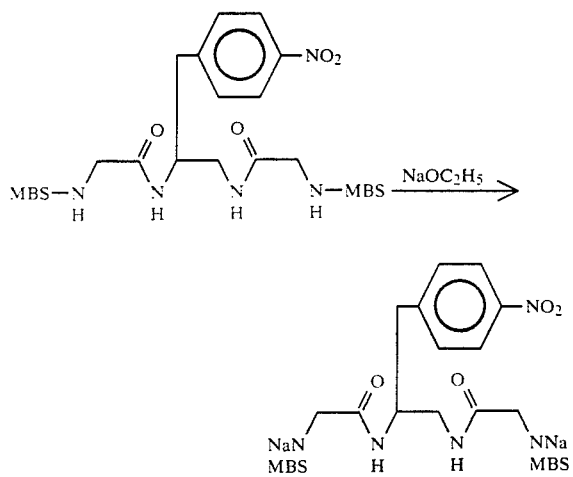

0.13 g Na were dissolved in 10 ml EtOH. 1.5 g of the tetraaza compound were partly dissolved in 150 ml dry ethanol and the NaOC₂H₅-solution was added dropwise at room temperature. The mixture was stirred for 45 minutes, followed by refluxing for ½ hour. Then the solvent was removed under reduced pressure. The yield was 1.5 g or 96 percent.

Step 8

Cyclization of 1,10-disodium-1,10-bis-(p-methoxybenzenesulfonyl)-5-(p-nitrobenzyl)-1,4,7,10-tetraazadecane-3,8-dione with ethylene glycol ditosylate to 1,10-bis-(methoxybenzenesulfonyl)-5-(p-nitrobenzyl)-1,4,7,10-tetraazacyclododecane-3,8-dione

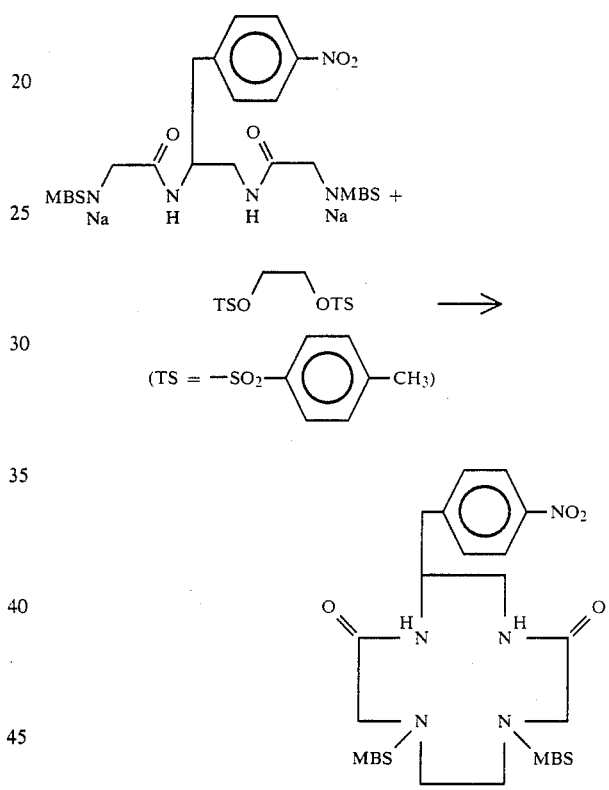

2.7 m moles of the tetraaza compound were dissolved in 20 ml DMF at 90° C. A solution of 1 g ethylene glycol ditosylate (prepared from ethylene glycol and p-toluenesulfonyl chloride in pyridine, followed by workup with 2N HCl/CH₂Cl₂) in 10 ml DMF was added dropwise at 90° C. The mixture was stirred at this temperature for 3 hours. After cooling to room temperature, 40 ml H₂O were added until the solution started clouding. After 4 hours of stirring at room temperature, the brown precipitate was filtered off, washed with water, and vaccum-dried. More precipitate can be obtained by adding more water to the solution under continuous stirring. The yield was 390 mg or 21 percent. The product was characterized by ¹H-nmr.

Step 9

Borane-reduction of 1,10-bis-(methoxybenzenesulfonyl)-5-(p-nitrobenzyl-1,4,7,10-tetraazacyclodecane-3,8-dione to the corresponding diamine

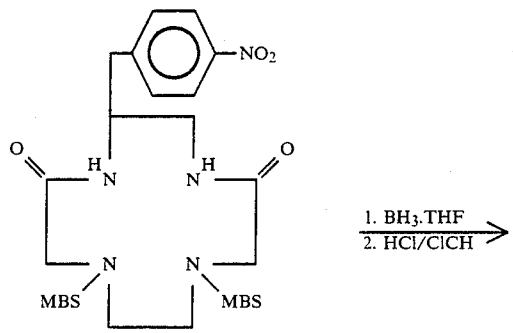

1. BH₃·THF
2. HCl/ClCH

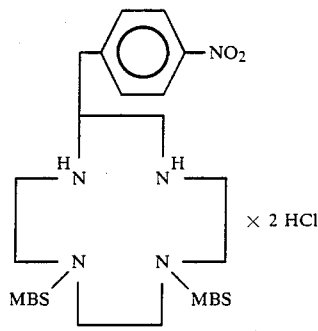

× 2 HCl 390 mg of the diamide were dissolved in 100 ml tetrahydrofurane (THF) and, at 0° C., 1.4 ml 1M BH₃ THF were added under exclusion of water. The mixture was then heated to reflux and refluxed for 3 hours, then the solvent was rotaevaporated. The residue was treated with 50 ml methanol, the solvent was removed under reduced pressure, the residue taken up into CH₃OH again and the same procedure repeated twice. Finally, the residue was taken into 5 ml dry ethanol and treated with gaseous HCl for 1 hour (cooled flask, reflux). The mixture was then refluxed for 20 hours, followed by cooling to 0° C. and resaturation with HCl gas. Some precipitate formed upon refrigeration, wax was obtained by concentrating the solution. The product was washed/recrystallized from ethanol and vaccum-dried. The yield was 310 mg or 99 percent. Characterization by ¹H-nmr.

Step 10
Deprotection of 1,10-bis-(p-methoxybenzenesulfonyl)-5-(p-nitrobenzyl)-1,4,7,10-tetraazacyclododecane dihydrochloride with methanesulfonic acid and amisole to 2-(p-nitrobenzyl)-1,4,7,10-tetraazacyclododecane (2-pNo₂ bzcyclen)

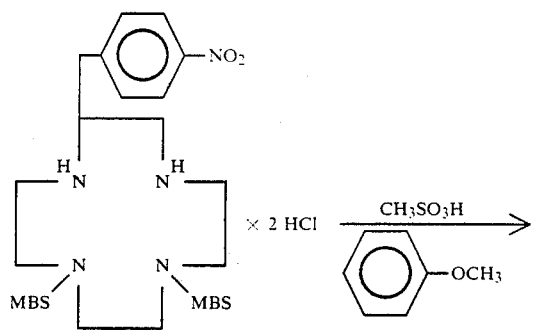

× 2 HCl $\xrightarrow{CH_3SO_3H}$

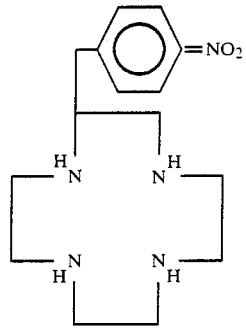

290 mg of the protected cycle was put into a mixture of 3.5 ml methanesulfonic acid (MSA) and 0.18 ml amisol and stirred at 90° C. for 20 hours. After cooling to room temperature, the mixture was extracted three times with diethyl ether, followed by treatment with 20 ml H₂O/HCl (pH 2), extracted three more times with ether and run over a large molar, excess of Bio Rad Ag 1×8 column (OH-form, anion exchanger). Two fractions of about 40–50 mg each (dissolved solid) were obtained (color yellow to light brown). 500 MHz-¹H-nmr in acidic acid basic D₂O showed that both fractions were the pure product.

Step 11 - Step 9
Alkylation of 2-(p-nitrobenzyl)-1,4,7,10-tetraazacyclododecane with bromacetic acid to 2-(p-nitro-benzyl)-1,4,7,10-tetraazacyclodocecane-1,4,7,10-tetraacetic acid (pNO₂-DOTA).

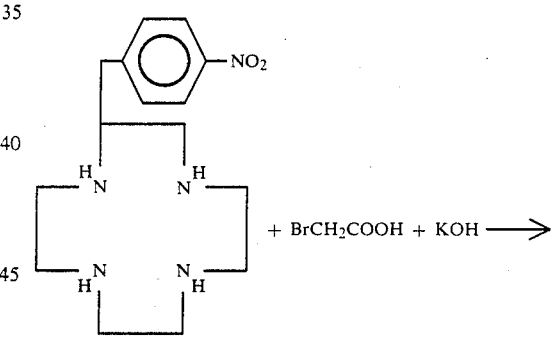

+ BrCH₂COOH + KOH ⟶

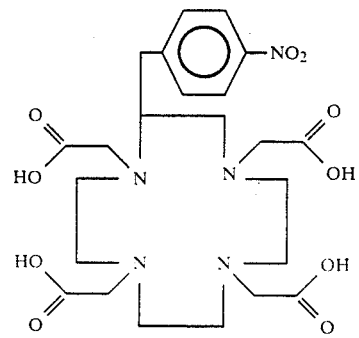

500 mg of the cyclen compound were dissolved in 15 ml H₂O and 0.61 g bromoacetic acid and 0.58 g potassium hydroxide (85 percent) were added at room temperature. The solution was stirred at 75° C. for 20 hours. After addition of another 1.21 g bromoacetic acid and another 1.16 g KOH, the mixture was again stirred at 75° C. for 20 hours. It was cooled to room temperature and acidified to pH 2.5 with 0.5N HCl. Total solution volume 40 ml. The solution was run over a threefold molar excess of AG50W×8 (H+-form) cation exchange resin (Bio Rad), the column washed with water until neutral and Cl/Br-free. Then the product was eluted with 1.7N aqueous ammonia. The solvent was rotaevporated slowly at room temperature and the residue freeze-dried by HPLC (reverse phase, methanol/phosphate buffer gradient, UV-detection 360 nm), two main factors (elution times 10 and 11 minutes at 3 ml/mm) were obtained, one of which (35 mg) was the derived DOTA, the other (55 mg) was the starting material. Characterization of the products by 500 MHz 1H-nmr and $^{252}$Cf-PDMS after removal of the HPLC buffer by another run over AG50W×8.

Steps 12 and 13

Reaction of 2-(p-nitrobenzyl)-1,4,7,10-tetraazacyclododecane-1,4,7,10-tetraacetic acid with H$^2$/Pd/C and further with thiophosgene to 2-(p-isothiocyanatobenzyl)-1,4,7,10-tetraazacyclododecane-1,4,7,10-tetraacetic acid

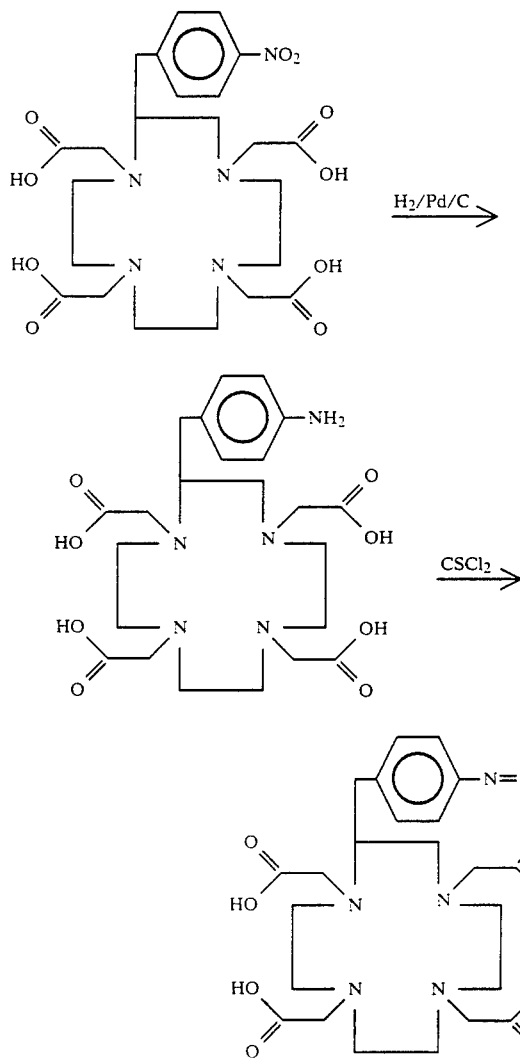

10 percent Pd on C-catalyst were suspended in 3 ml H$_2$O and, at 4° C., treated with H$_2$ gas until saturated. Then, a solution of pNO$_2$ bz DOTA (30 mg) in aqueous ammonia (pH10) was added via a syringe and the system was filled with a slight overpressure of H$_2$ gas. After 6 hours, 4 ml H$_2$ were used up. After several filtrations, the clear yellow product was obtained by freeze-drying of the solution. $^1$H-nmr spectra of the solid product in D$_2$O showed the pure p-amino compound. The yield was 27 mg or 95 percent. A $^{252}$Cf-PDMS showed the product. The product was dissolved in 3 ml H$_2$O/6 mg Na$_2$CO$_3$ and, under vigorous stirring, a solution of 4.8 ml CSCl$_2$ in 2 ml CHCL$_3$ was added dropwise at room temperature. After stirring at room temperature for another 6 hours, another 451 thiophogene in 1 ml CHCl$_3$ were added as was more sodium carbonate to keep the pH around 8. After 20 hours, a fluorescamine test showed no more p-NH$_2$ compound. A tlc on silica gel, element CH$_3$CN: H$_2$O: HCONH$_2$ 30:10:0.3, gave one spot for the product at Rf=0.4. The mixture was stripped over a florasil column in CH$_3$CN:H$_2$O30:8, where a gooey brown residue stayed on the column while the colorless product, containing little in organic salt, was eluted and freeze-dried. The yield was 31 mg or 99.9 percent. Characterization by 1H-nmr $^{252}$Cf-PDMS and elemental analyses.

What is claimed is:

1. A method of producing a compound of the formula:

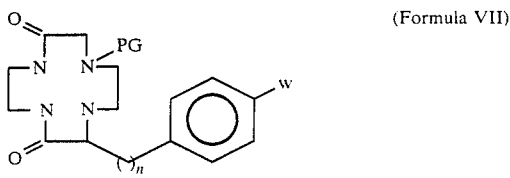

(Formula VII)

comprising the steps of:

(1) reacting, in dilute anhydrous solution, a compound of the formula:

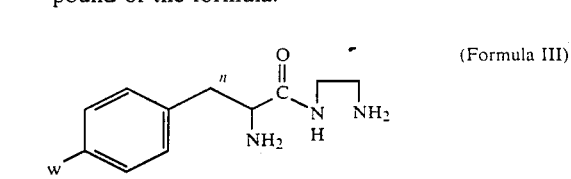

(Formula III)

wherein n is an integer from 1 to 5, w is a member selected from the group consisting of —NO$_2$, —COOH, —OCH$_2$OOCH$_3$, with a compound of the formula:

(Formula VI)

wherein PG is a carbamate amino protecting group and E is a leaving group; and (2) extracting the compound of formula I from the reaction mixture.

2. The process of claim 1 wherein said protecting group is an alkyl or aryl substituted carbamate.

3. The process of claim 1 wherein said leaving group is a hydroxylamine derivative, a substituted phenol derivative, or a mixed anhydride.

4. A method of claim 1 wherein the extraction of step (2) is accomplished by:

(1) drying the reaction mixture from step (1) of claim 1 and (2) extracting the compound of formula (VII) using a biphasic mixture of water and an organic solvent, wherein the compound of formula (VII) is dissolved in the organic solvent.

5. A method of claim 1 wherein, additionally, the compound of formula VII is reduced to provide a compound of the formula:

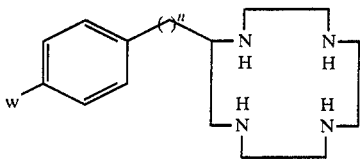

(Formula IX)

6. A method of claim 5 wherein the reduction is accomplished by the steps of:
 (1) dissolving the compound of formula VII in trifluoroacetic acid and allowing the resulting mixture to react for about three hours;
 (2) evaporating the resulting reaction mixture;
 (3) Precipitating the product in ethyl acetate; and
 (4) Reducing the product obtained in step (3) with $BH_3$ in THF.

* * * * *